(12) United States Patent
Suetsugu

(10) Patent No.: US 12,041,403 B2
(45) Date of Patent: Jul. 16, 2024

(54) COVER FOR MICROPHONE-EQUIPPED EARPHONE

(71) Applicant: Katsunori Suetsugu, Tokyo (JP)

(72) Inventor: Katsunori Suetsugu, Tokyo (JP)

( * ) Notice: Subject to any disclaimer, the term of this patent is extended or adjusted under 35 U.S.C. 154(b) by 765 days.

(21) Appl. No.: 17/229,380

(22) Filed: Apr. 13, 2021

(65) Prior Publication Data

US 2021/0345030 A1 Nov. 4, 2021

(30) Foreign Application Priority Data

May 1, 2020 (JP) ................................ 2020-081068

(51) Int. Cl.
*H04R 1/08* (2006.01)
*H04R 1/10* (2006.01)
*A61F 11/14* (2006.01)

(52) U.S. Cl.
CPC ........... *H04R 1/086* (2013.01); *H04R 1/1016* (2013.01); *H04R 1/105* (2013.01); *A61F 11/14* (2013.01); *H04R 2420/07* (2013.01)

(58) Field of Classification Search
CPC ...... H04R 1/086; H04R 1/1016; H04R 1/105; H04R 5/033; H04R 2420/07; A61F 11/14
See application file for complete search history.

(56) References Cited

U.S. PATENT DOCUMENTS

| | | | |
|---|---|---|---|
| 4,250,877 A | 2/1981 | Owens et al. | |
| 9,774,943 B1 * | 9/2017 | Weitzner | H04R 1/105 |
| 10,542,339 B1 * | 1/2020 | Ruth | H04R 1/08 |
| 10,547,923 B1 | 1/2020 | Miller | |
| 2018/0070668 A1 | 3/2018 | Stephens | |

FOREIGN PATENT DOCUMENTS

| | | |
|---|---|---|
| CN | 204949598 U | 1/2016 |
| CN | 105763697 A | 7/2016 |
| CN | 107405508 A | 11/2017 |
| JP | 3076219 U | 3/2001 |
| JP | 2018-028652 A | 2/2018 |
| KR | 10-2009-0048931 A | 5/2009 |
| KR | 10-2019-0138151 A | 12/2019 |

OTHER PUBLICATIONS

Japanese Office Action, mailed Jan. 12, 2021, for Japanese Patent Application No. 2020-081068, 10 pages (with English translation).

* cited by examiner

*Primary Examiner* — Tuan D Nguyen
(74) *Attorney, Agent, or Firm* — Apex Juris, pllc; Hilde M. L. Coeckx

(57) ABSTRACT

A cover for microphone-equipped earphone having a microphone integral to an earphone used for communication equipment includes: a mouth-ear cover for covering a mouth while allowing speaking and covering one-side ear inserted with the earphone, wherein the mouth-ear cover having mouth and ear cover sections is configured such that: an internal space defined by the mouth cover section has a substantially hemispherical shape capable of covering the mouth, and has an edge of an opening capable of closely contacting a periphery of the mouth; an internal space defined by the ear cover section has a substantially semi-oval spherical shape capable of covering the one-side ear, and has an edge of an opening capable of closely contacting a periphery of the one-side ear; and the internal spaces defined by the mouth and ear cover sections are capable of communicating with each other via a voice passage through which voice is conveyable.

18 Claims, 17 Drawing Sheets

COVER FOR MICROPHONE-EQUIPPED EARPHONE

CROSS REFERENCE TO RELATED APPLICATIONS

This application claims the benefit of priority under the Paris Convention upon Japanese Patent Application No. 2020-081068, filed on May 1, 2020, of which full contents are incorporated herein by reference.

BACKGROUND OF THE INVENTION

Field of the Invention

A cover for microphone-equipped earphone according to the present invention relates to a cover for microphone-equipped earphone to be used for communication equipment. The cover for microphone-equipped earphone is configured such that, when a user wears the cover to cover the mouth while allowing speaking arranged with a microphone of the microphone-equipped earphone and further wears an earphone of the microphone-equipped earphone at the ear, the user's voice from the mouth could be picked up by the microphone without any leakage of the voice to the outside.

The communication equipment in the present invention is equipment or devices having communication functions such as mobile phones, smartphones, iPad (registered trademark), notebook and desktop computers, smart speakers, and the like.

Further, the microphone-equipped earphone includes peripheral equipment, connected electrically to e.g. a smartphone with or without wires in recent years, to be used for talking through the use of the smartphone as a main unit by the user while having his or her main-unit smartphone in a bag or pocket, i.e., without holding his or her main-unit smartphone with the hand. The microphone-equipped earphone includes one having a microphone and an earphone separated from each other as different units, i.e., a separate-type microphone-equipped earphone, and another having a microphone and an earphone integral to each other, i.e., an integral-type microphone-equipped earphone.

Description of the Background Art

To the present inventor's knowledge, there has not existed any conventional cover for microphone-equipped earphone, which is arranged with a microphone, and configured to cover the mouth while allowing speaking of a user without any leakage of the user's voice from the mouth to the outside.

Problems to be Solved

In making a talk on e.g. a smartphone, by using a microphone-equipped earphone fitted in the ear of a user, the user had the advantages that he or she could talk in a hands-free state without the need of holding the smartphone with the hand. In such a case, however, while a counterpart's voice could be heard by the user from the earphone fitted in the ear without any leakage to the surroundings, the user's voice has been leaked to the surroundings, which has resulted in disabling confidential talking. In addition, the presence of noise or unwanted sound in the surroundings has caused the inconveniences that the user's voice might be lost in the noise or unwanted sound to be conveyed incorrectly to the counterpart.

For this reason, in making a confidential talk or in the presence of noise or unwanted sound, there has been a need to seek a quiet place such as a place among buildings, a telephone booth, a conference room, or the like, and make a talk in such a place.

SUMMARY OF THE INVENTION

In order to solve the above-described technical problems, there is provided a cover for microphone-equipped earphone allowing a user's voice to be conveyed to a counterpart without causing any leakage to the surroundings and without picking up any noise or unwanted sound in the surroundings.

Means for Solving Problems

A first aspect of the present invention is a cover for microphone-equipped earphone having a microphone integral to an earphone to be used for communication equipment, the cover comprising: a mouth-ear cover for covering a mouth while allowing speaking of a user as well as covering one-side ear of the user into which the earphone is to be inserted, wherein the mouth-ear cover having a mouth cover section and an ear cover section is configured such that: an internal space defined by the mouth cover section of the mouth-ear cover has a substantially hemispherical shape capable of covering the mouth of the user, and has an edge of an opening thereof capable of closely contacting a periphery of the mouth; an internal space defined by the ear cover section of the mouth-ear cover has a substantially semi-oval spherical shape capable of covering the one-side ear of the user, and has an edge of an opening thereof capable of closely contacting a periphery of the one-side ear; and the internal space defined by the mouth cover section and the internal space defined by the ear cover section are capable of communicating with each other via a voice passage through which voice of the user is conveyable therebetween.

A second aspect of the present invention is the cover for microphone-equipped earphone in the first aspect, wherein the voice passage has a semicircular shape, in cross section transverse to a longitudinal direction thereof, whose both ends are capable of abutting on a face of the user.

A third aspect of the present invention is the cover for microphone-equipped earphone in the first aspect, wherein the voice passage has a tubular shape penetrating an interior of a cover member of said cover.

A fourth aspect of the present invention is the cover for microphone-equipped earphone in any one of the first to third aspects, wherein the mouth-ear cover has a hook, to be hooked on an upper end of the one-side ear of the user, provided at an upper end of the internal space defined by the ear cover section.

A fifth aspect of the present invention is the cover for microphone-equipped earphone according to any one of the first to third stages, further comprising: a headphone-type band-like engagement tool to be worn by the user across a parietal region to reach a position near the other-side ear of the user.

A sixth aspect of the present invention is the cover for microphone-equipped earphone according to any one of the first to third stages, further comprising: a glass-temple-like engagement tool extending from the mouth cover section to be hooked on the other-side ear of the user.

A seventh aspect of the present invention is the cover for microphone-equipped earphone according to any one of the first to third stages, further comprising: a mask-string-like engagement tool extending from the mouth cover section to be hooked on the other-side ear of the user.

An eighth aspect of the present invention is the cover for microphone-equipped earphone according to any one of the first to seventh stages, further comprising: a pinching projection arranged to project from an external surface of the mouth cover section.

Advantageous Effects of the Invention

According to any one of the first to eighth aspects of the present invention, there could be provided a cover for microphone-equipped earphone allowing voice generated by a user to be conveyed confidentially and correctly to a counterpart without causing any leakage to the surroundings and without any interference by noise or unwanted sound in the surroundings.

According to the fourth aspect of the present invention, the mouth-ear cover, as the cover for microphone-equipped earphone, could be worn by the user stably on the ear.

According to the fifth to seventh aspects of the present invention, the cover for microphone-equipped earphone could be worn by the user stably on both of the ears, thereby allowing both hands to be used freely.

BRIEF DESCRIPTIONS OF THE DRAWINGS

DESCRIPTIONS OF EMBODIMENTS OF THE INVENTION

As the best mode for carrying out a cover for microphone-equipped earphone, a mouth cover will be described with reference to FIGS. 1 to 5 showing EXAMPLE 1, and a mouth-ear cover will be described with reference to FIGS. 6 to 17 showing EXAMPLE 2. It is to be noted that a state where a user indicated by phantom lines wears the cover for microphone-equipped earphone of is shown in each of FIGS. 2 to 17.

EXAMPLE 1

Figure 1:
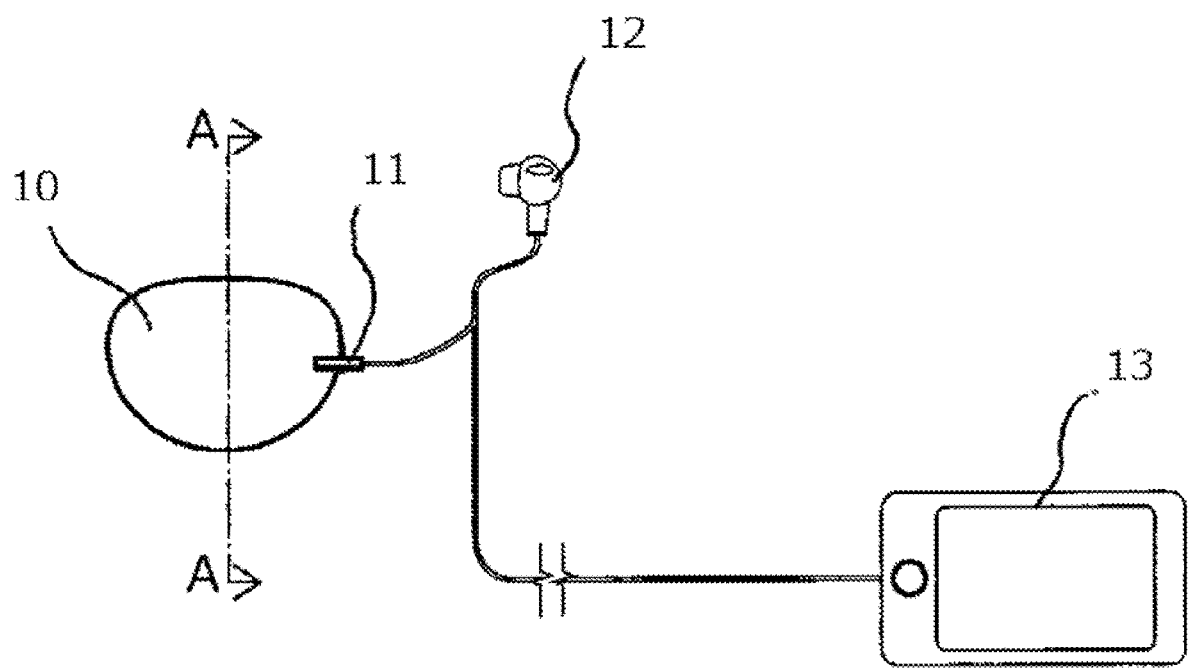
FIG. 1 depicts a schematic view of a mouth cover according to EXAMPLE 1.

A cover for microphone-equipped earphone shown in each of FIGS. 1 to 5 is a mouth cover 10 for covering only a mouth while allowing talking of a user. FIG. 1 depicts a schematic view of an example system for a separate-type microphone-equipped earphone in which: a microphone 11, which is provided as a separate and different unit from an earphone 12 to be worn by a user at one-side ear by insertion into the one-side ear, is arranged at the mouth cover 10 configured to cover a mouth while allowing talking of the user; a smartphone 13, which serves as communication equipment, is provided as main equipment; and these units are connected to each other with wires.

Figure 2:
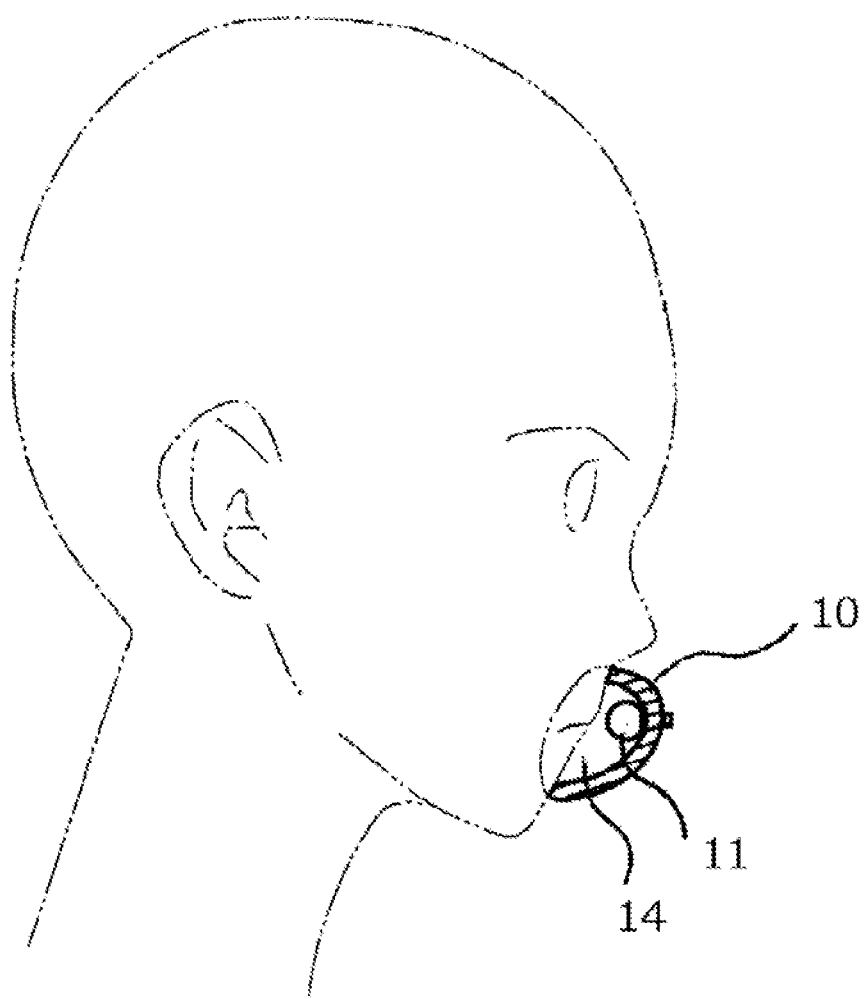
FIG. 2 depicts a cross-sectional view as taken along the line A-A in FIG. 1.
Figure 3:
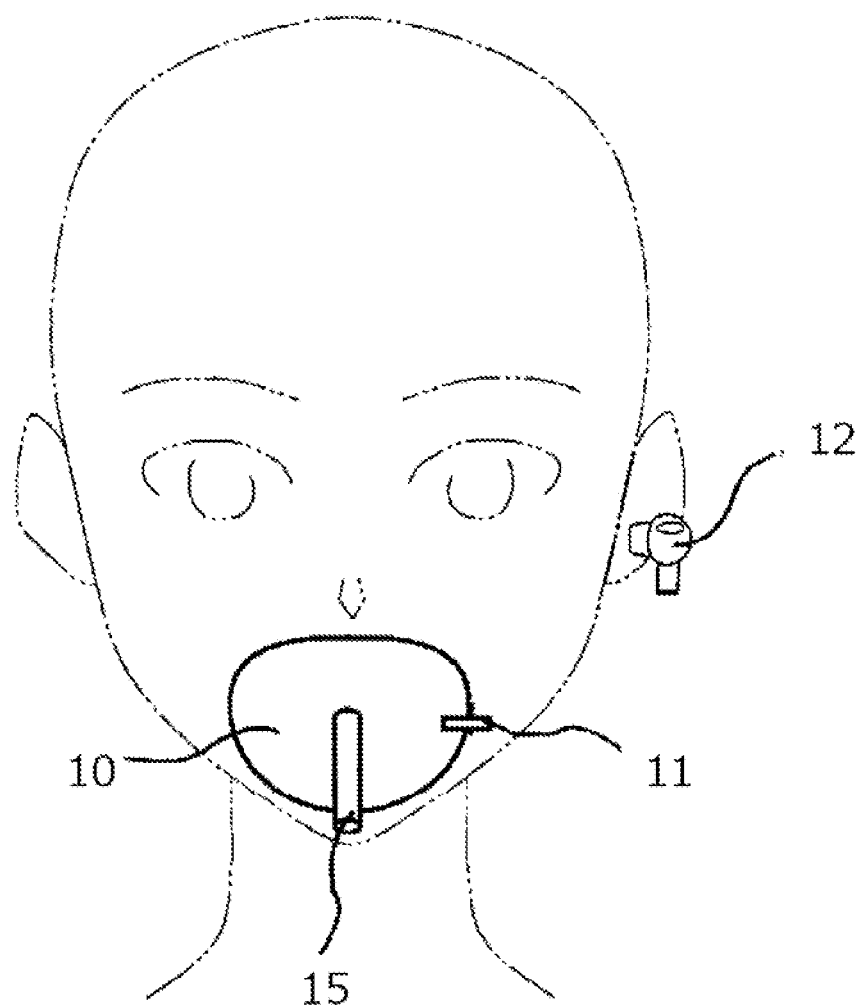
FIG. 3 depicts a front view of the mouth cover according to EXAMPLE 1 arranged with a pinching projection.

FIGS. 2 and 3 show an example system, which has units connected to each other without wires, different from the above example system having units connected to each other with wires shown in FIG. 1. These examples are applicable to any of a system of communication equipment formed by wired connection and a system of communication equipment formed by wireless connection, and are also applicable irrespective of whether a communication system uses bone-conduction means or not.

The mouth cover 10 shown in FIG. 2, having a substantially hemispherical shape as a whole, is configured such that an edge of the substantially hemispherical shape is capable of being in substantially close contact with a periphery of the mouth of the user, thereby to prevent leakage of voice generated from the mouth. Leakage of the voice is not required to be prevented completely but required to be prevented to such an extent that the voice leaked to the outside from the mouth cover 10 is not distinguishable in meaning for others in the outside when the voice reaches the others' ears.

It is essential that the content of a talk be prevented from being disclosed to the outside. For this purpose, the configuration of the mouth cover 10 is required at least to cover the mouth while allowing speaking of the user, and the configuration and material thereof are not necessarily further limited. The mouth cover 10 may be made of material not particularly limited; e.g., it may be appropriate to form the mouth cover 10 of synthetic resin.

As shown in FIGS. 2 to 5, the microphone 11 of EXAMPLE 1 is arranged such that an input part thereof is present inside an internal space 14 defined by the mouth cover 10. However, this is merely an example, and the arrangement of the microphone 11 at the mouth cover 10 is not limited to such an example. It is essential that the microphone 11 be arranged at an appropriate position allowing receipt of the user's voice generated from the mouth.

The mouth cover 10 shown in FIG. 3 as the cover for microphone-equipped earphone has a pinching projection 15 arranged on an external surface of the mouth cover 10 for retaining the mouth cover 10 in a state of abutting on the mouth with a hand of the user. The mouth cover 10 shown in FIG. 1 is arranged with such a pinching projection. Therefore, in contrast to a case where the mouth cover 10 is to be used while being pressed against the mouth with a hand or fingertip of the user at an appropriate position on the surface thereof, such a pinching projection thus arranged allows the mouth cover 10 to be pressed stably against the mouth.

Figure 4:
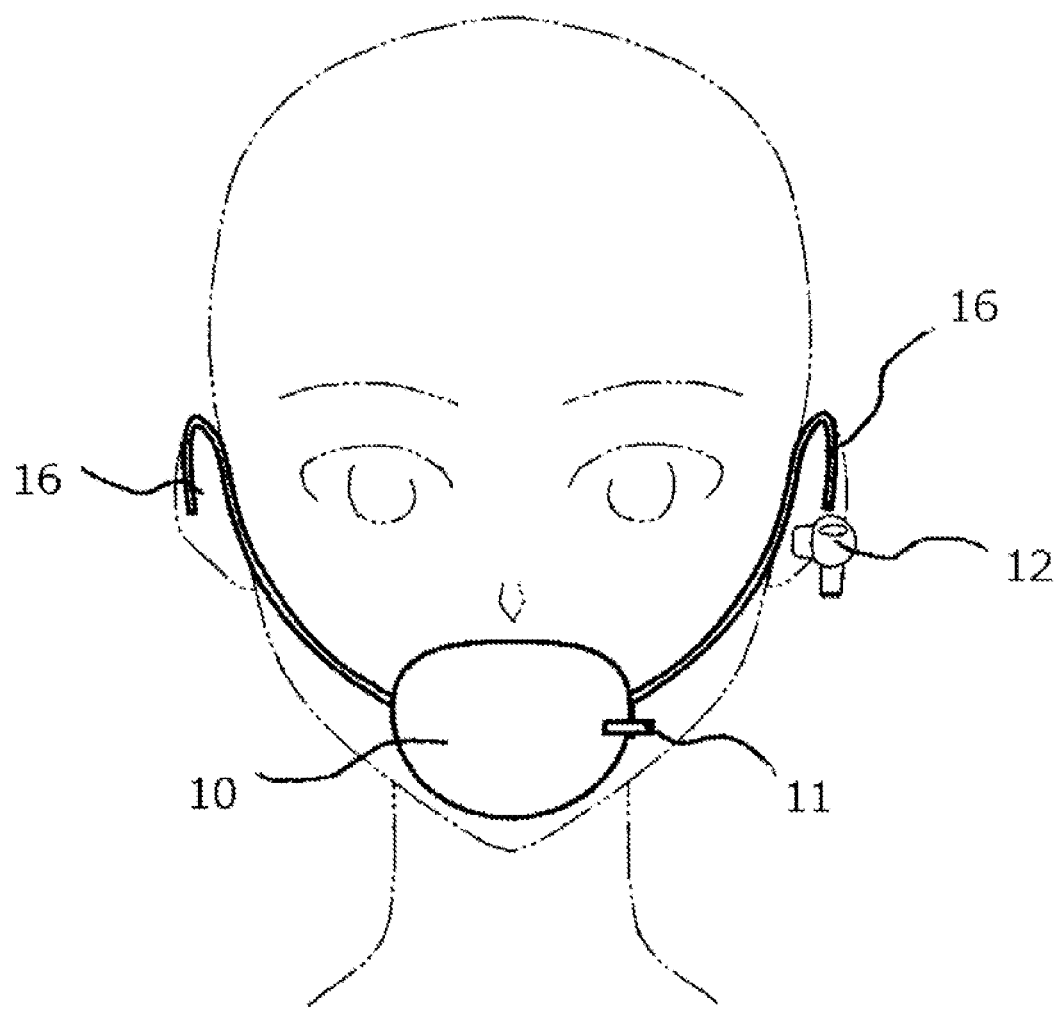
FIG. 4 depicts a front view of the mouth cover according to EXAMPLE 1 provided with a pair of glass-temple-like engagement tools.

The mouth cover 10 shown in FIG. 4 as the cover for microphone-equipped earphone has glass-temple-like engagement tools 16 extending from both sides of the mouth cover 10 to be hooked on right-side and left-side ears of the user. Because the above-described mouth cover 10 shown in FIGS. 1 and 3 is required to be pressed by the user against the mouth with the hand or fingertip, at least one of the user's hands is prohibited from being used freely. By contrast, as a result of the mouth cover 10 shown in FIG. 4 making both of the user's hands free, some work could be done by the user with both hands during making communication.

Figure 5:
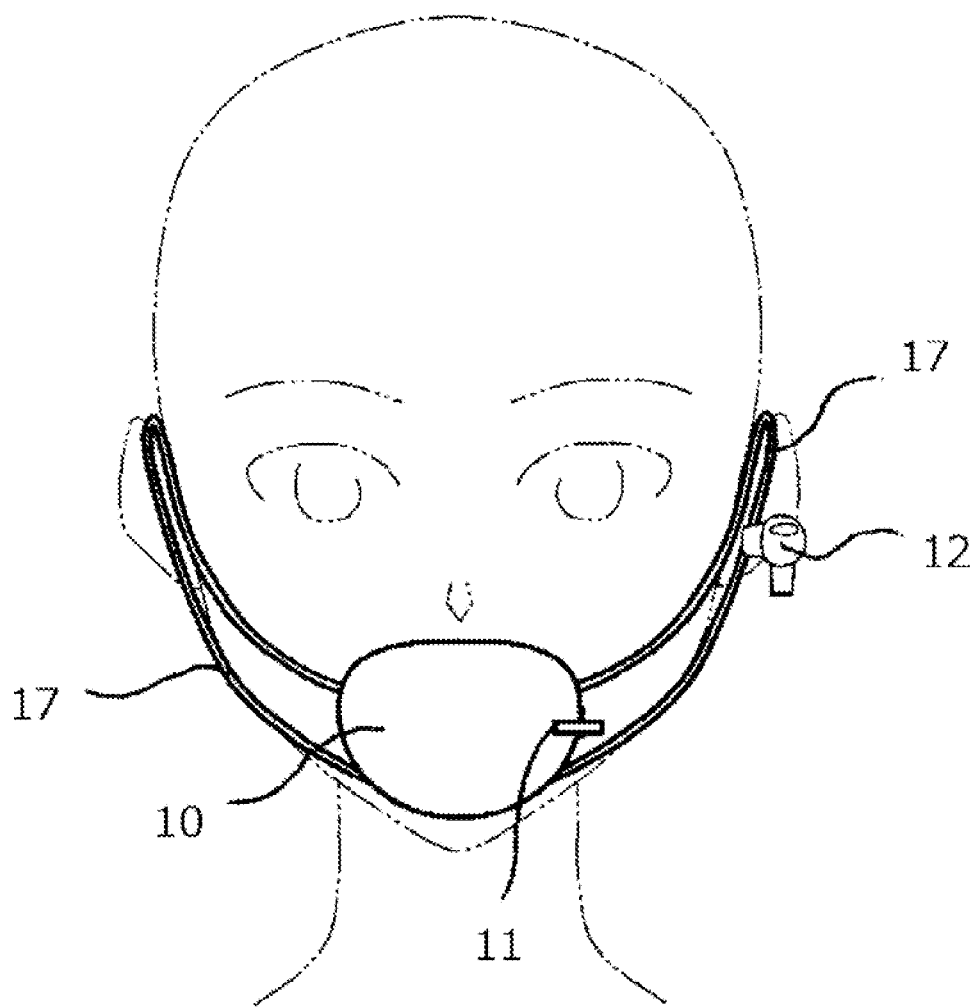
FIG. 5 depicts a front view of the mouth cover according to EXAMPLE 1 provided with a pair of mask-string-like engagement tools.

The mouth cover 10 shown in FIG. 5 as the cover for microphone-equipped earphone has mask-string-like engagement tools 17 extending from both sides of the mouth cover 10 to be hooked on right-side and left-side ears of the user. In a similar manner to the above-described mouth cover 10 shown in FIG. 4, the mouth cover 10 shown in FIG. 5 making both of the user's hands free, which is different from a case of the mouth cover 10 shown in FIGS. 1 and 3, some work could be done by the user with both hands during making communication.

EXAMPLE 2

A cover for microphone-equipped earphone shown in each of FIGS. 6 to 17 is a cover (100) having a mouth cover (20) substantially similar to the above-described mouth cover 10 of EXAMPLE 1, and an ear cover section 21, integral to the mouth cover (20), extending from one of right and left sides of the mouth cover (20) (the left side of a user in FIGS. 6 to 17) along the cheek (left cheek in FIGS. 6 to 17) on the relevant side of the user (the left side of the user in FIGS. 6 to 17) so as to cover the ear (left ear in FIGS. 6 to 17) on the relevant side of the user (the left side of the user in FIGS. 6 to 17).

Hereinafter, for the convenience of description, the cover (100) of EXAMPLE 2 will be referred to as "mouth-ear cover 100"; a portion configured to cover the mouth of the user and a portion configured to cover the ear of the user out of the mouth-ear cover 100 will be referred to as a "mouth cover section 20" and an "ear cover section 21" respectively; and a portion of a band-like shape connecting between the mouth cover section 20 and the ear cover section 21 will be referred to as a "voice passage section 22."

A microphone-equipped earphone to be applied mainly with the cover (100) of EXAMPLE 2 is not the above-described separate-type microphone-equipped earphone of EXAMPLE 1 shown in FIG. 1 but an integral-type microphone-equipped earphone having a microphone integral to an earphone (not shown). The illustration of a state where such an integral-type microphone-equipped earphone is worn by the user by fitting in the ear is also omitted from each of FIGS. 6 to 17 (the illustrations of a microphone and an earphone are omitted).

Figure 6:
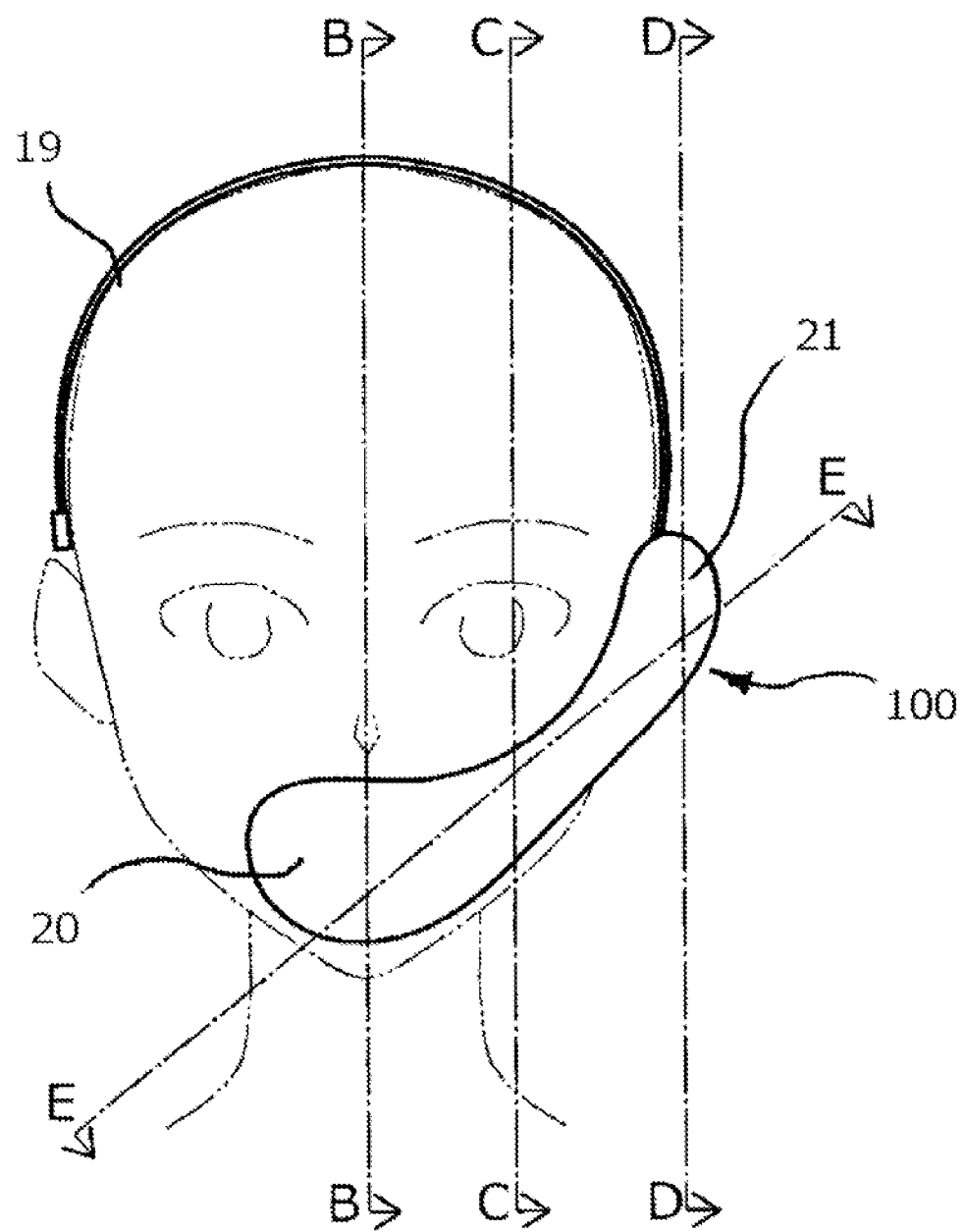
FIG. 6 depicts a front view of a mouth-ear cover according to EXAMPLE 2.
Figure 7:
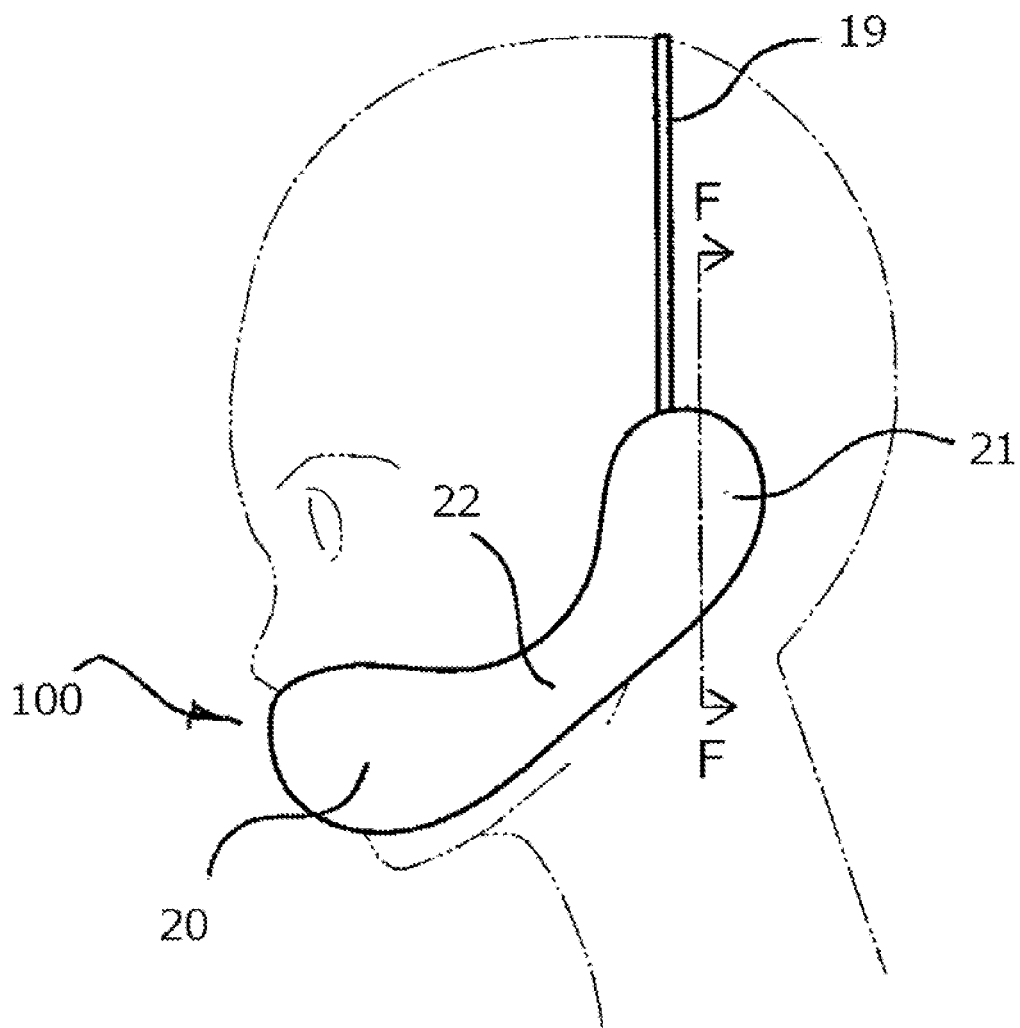
FIG. 7 depicts a right side view of the mouth-ear cover according to EXAMPLE 2.
Figure 8:
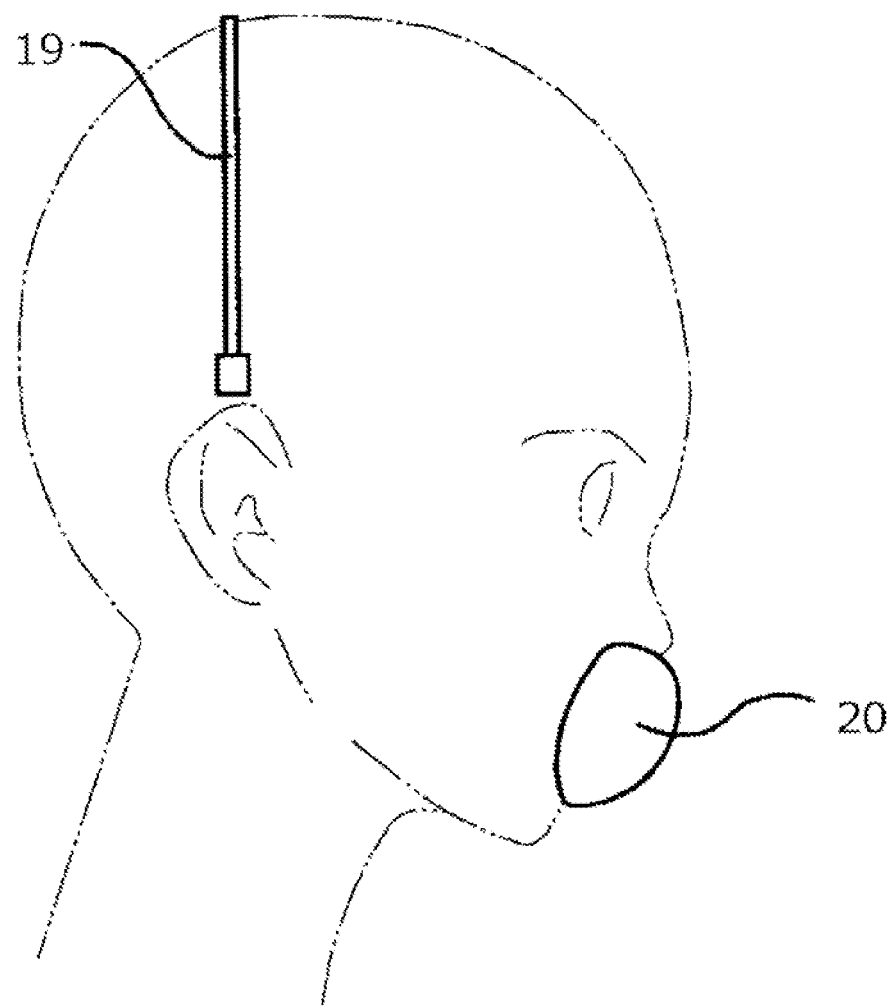
FIG. 8 depicts a left side view of the mouth-ear cover according to EXAMPLE 2.
Figure 9:
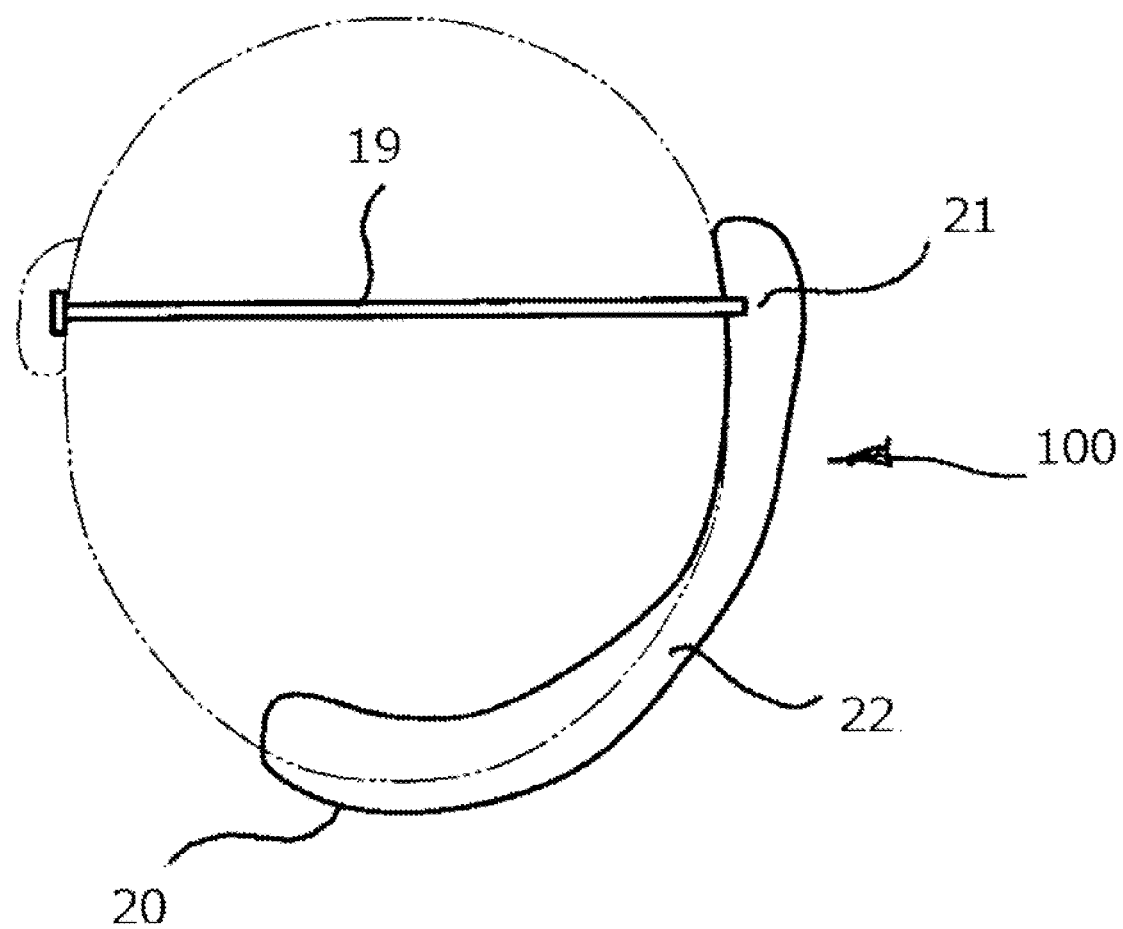
FIG. 9 depicts a plan view of the mouth-ear cover according to EXAMPLE 2.
Figure 10:
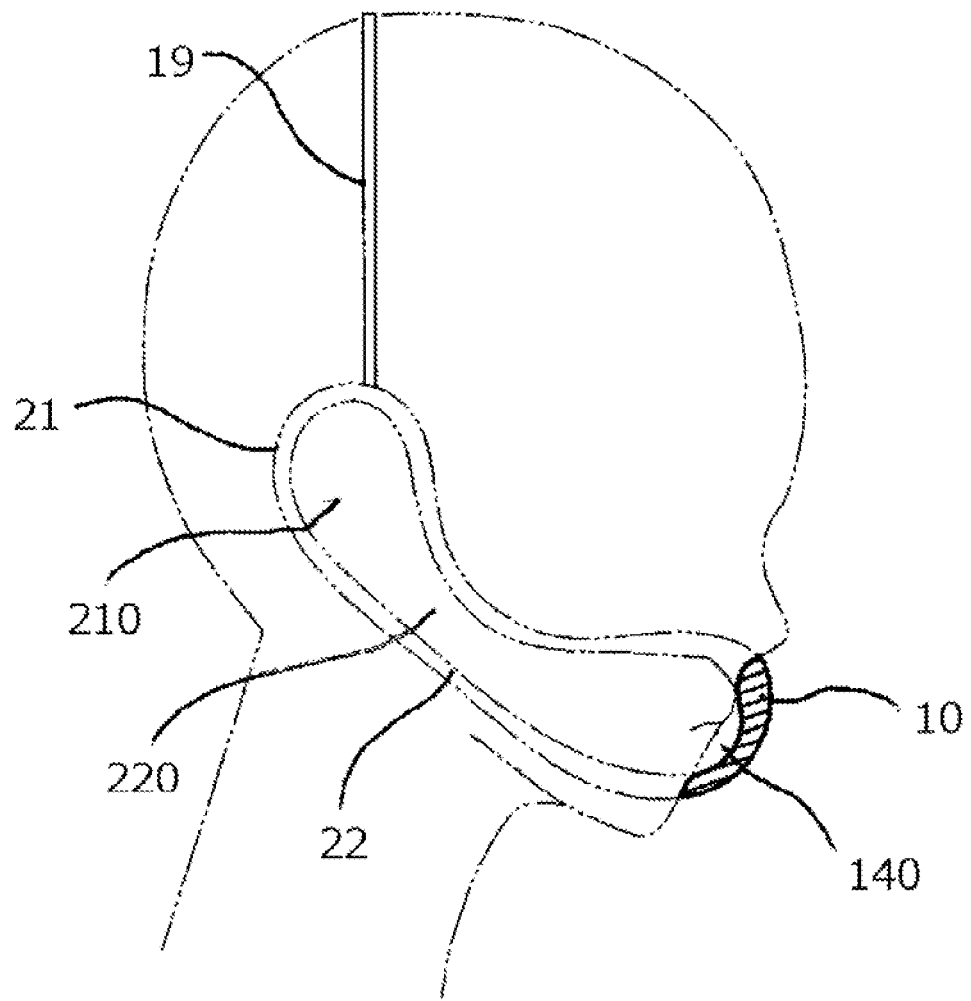
FIG. 10 depicts a sectional view as taken along the line B-B in FIG. 6.
Figure 11:
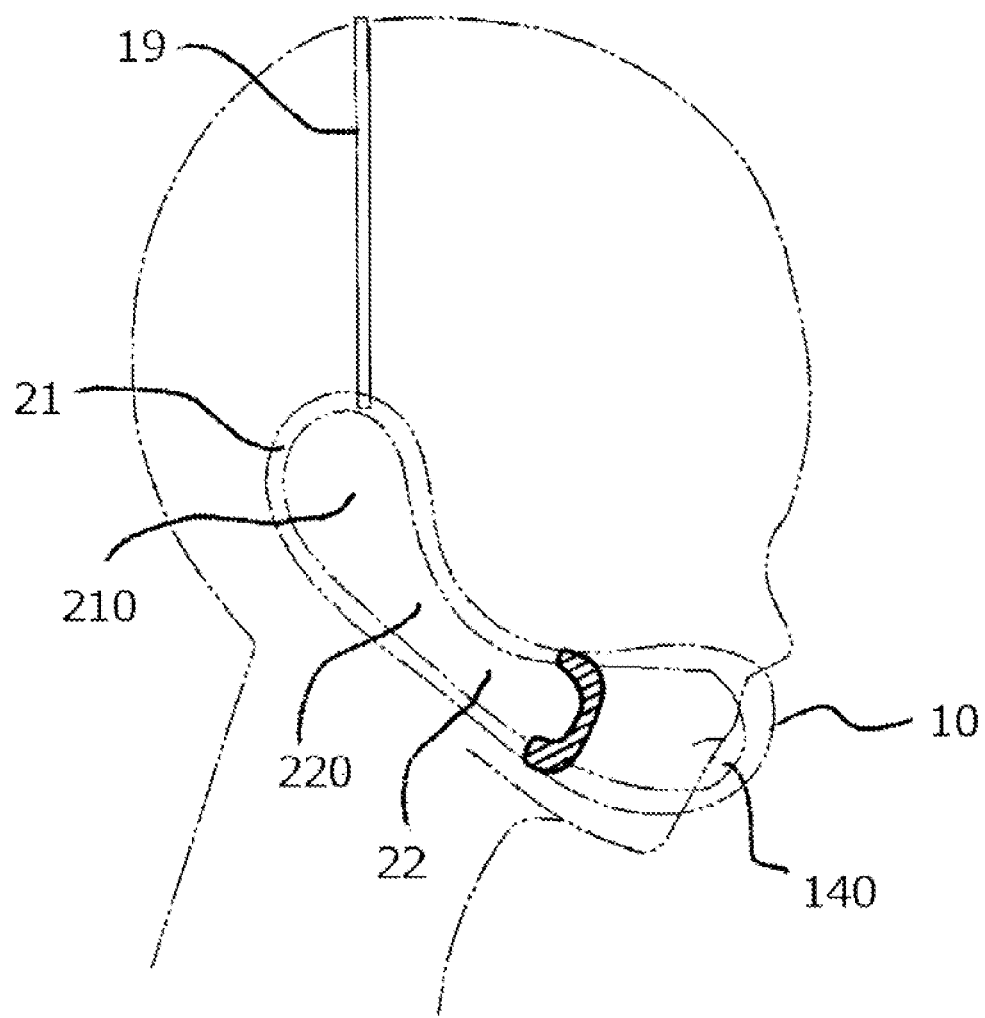
FIG. 11 depicts a sectional view as taken along the line C-C in FIG. 6.
Figure 12:
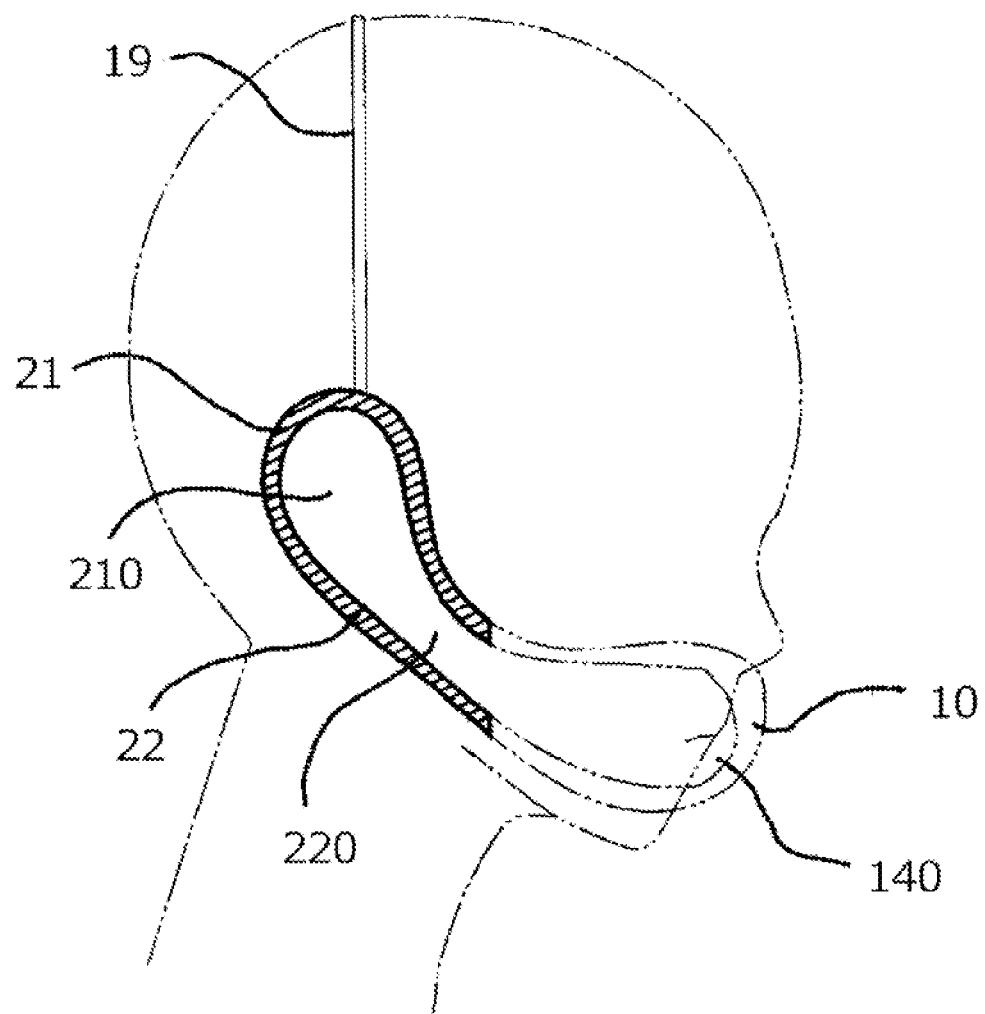
FIG. 12 depicts a sectional view as taken along the line D-D in FIG. 6.

As shown in FIGS. 6 and 7, between an internal space 140 defined by the mouth cover section 20 and an internal space 210 defined by the ear cover section 21 of the mouth-ear cover 100, the voice passage section 22 having a voice passage 220 is so formed in integral band-like shape as to communicate with each other, thereby to allow conveyance of the user's voice through the voice passage 220 defined by the voice passage section 22 therebetween.

In FIGS. 10 to 14, the internal space 140 defined by the mouth cover section 20 is a space of a substantially hemispherical shape configured to cover the mouth such that an edge of an opening of the space could closely contact a periphery of the mouth. Such an internal space 140 is required at least to be a space allowing talking of the user, and therefore, may have any shape as far as being sufficient for this purpose. The internal space 210 defined by the ear cover section 21 is a space of a substantially semi-oval spherical shape configured to cover the ear such that an edge of an opening of the space could closely contact a periphery of the ear. The internal space 210 may also have any shape as far as the internal space 210 allows voice generated from the mouth to pass through the voice passage 220, as will be described later, and thereafter reach a microphone of the microphone-equipped earphone (not shown) fitted in the ear.

The voice passage 220 defined by the voice passage section 22 has a semicircular shape in cross section transverse to a longitudinal direction thereof, and is configured such that both ends of the semicircular shape abut directly on a face, i.e., cheek surface of the user. The voice passage 220 may also have any spatial shape as far as the voice passage 220 allows voice generated from the mouth to reach the microphone of the microphone-equipped earphone (not shown) fitted in the ear. Alternatively, therefore, the voice passage 220 may be formed to be a hollow tube penetrating an interior of a member of the mouth-ear cover 100, i.e., may be formed into a simple tubular shape. Such a tube may have any inner diameter and shape.

Figure 13:
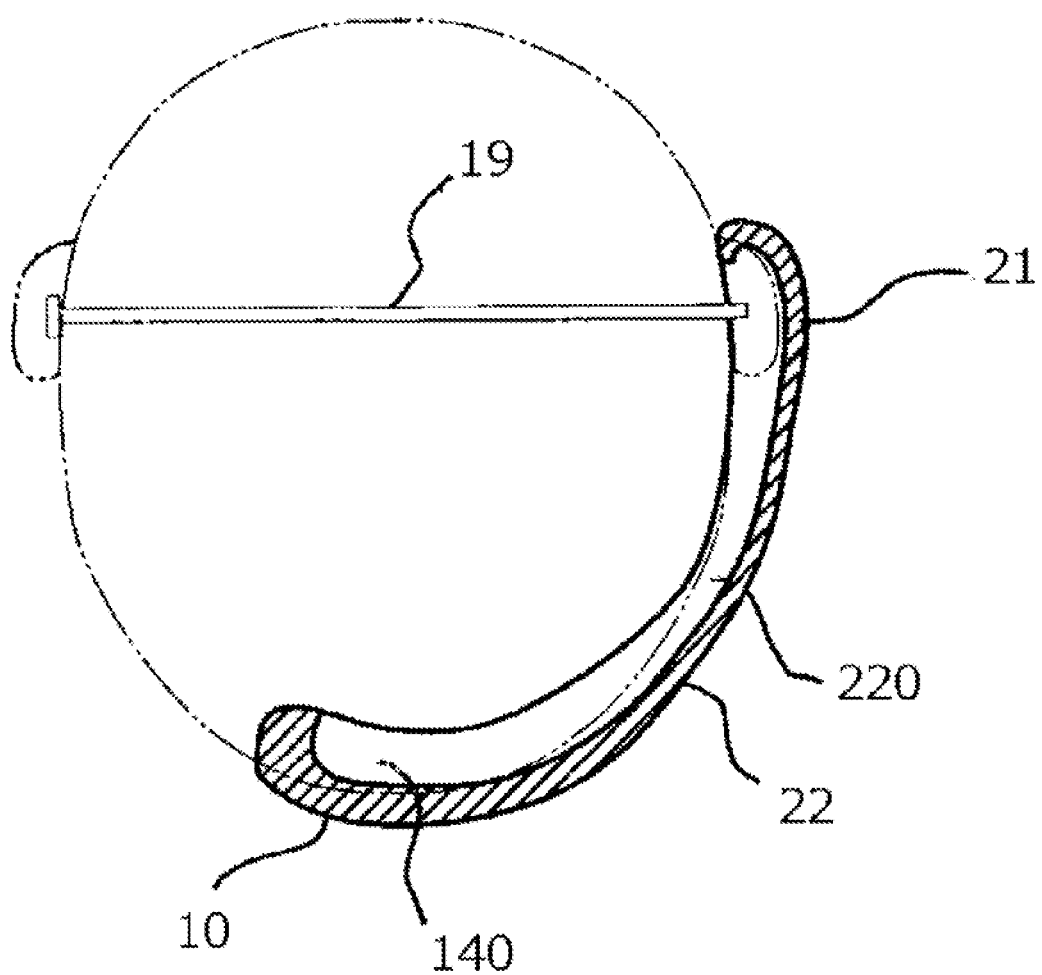
FIG. 13 depicts a sectional view as taken along the line E-E in FIG. 6.
Figure 14:
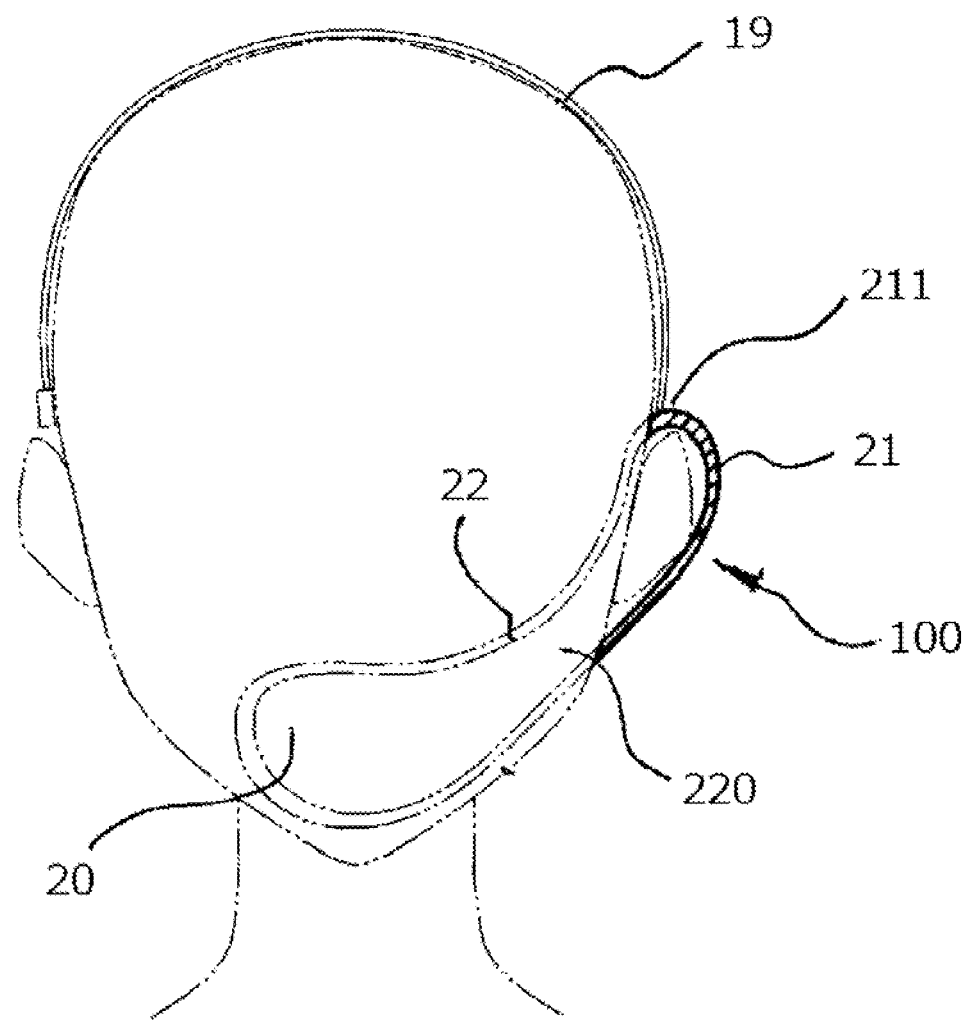
FIG. 14 depicts a sectional view as taken along the line F-F in FIG. 7.

In FIGS. 13 and 14, the ear cover section 21 has a hook 211 formed, at an upper end of the internal space 210 defined by the ear cover section 21, by bending a member As a result of hooking the hook 211 by the user on the upper end of the ear, a state of the mouth-ear cover 100 being fitted stably on the face (mouth and ear) at least on the ear side could be achieved when such a mouth-ear cover 100 is worn by the user.

Figure 15:
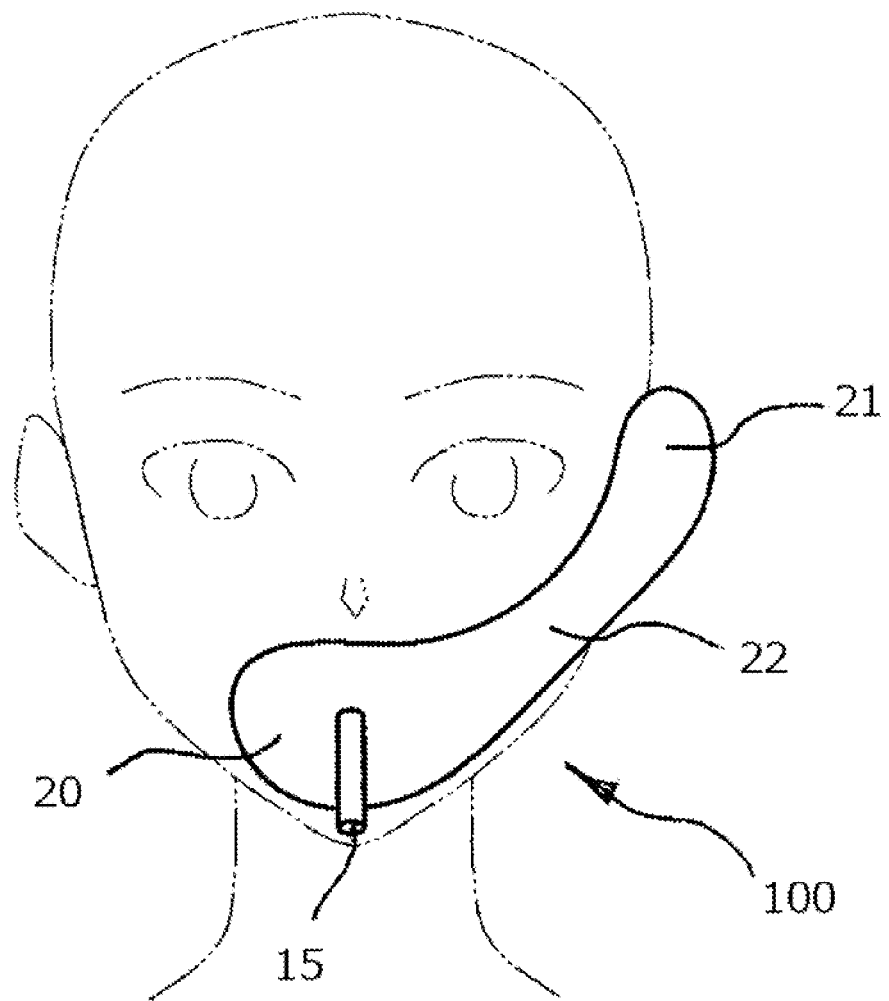
FIG. 15 depicts a front view of the mouth-ear cover according to EXAMPLE 2 arranged with a pinching projection.

In FIG. 15, a pinching projection 15 is arranged on an external surface of the mouth cover section 20 of the mouth-ear cover 100, as a cover for microphone-equipped earphone, for retaining the mouth-ear cover 100 in a state of abutting by the user on the mouth with the hand. Even when the mouth-ear cover 100 is to be pressed by the user against the mouth with the hand or fingertip at an appropriate position on the surface thereof, a state of the mouth-ear cover 100 being fitted stably on the mouth and the ear (face), i.e., a state of the mouth-ear cover 100 being pressed stably against the mouth and the ear (face) could be achieved as a result of the user's pinching the pinching projection 15 along with the user's wearing the above-described hook 211.

There still remains, however, the inconvenience in the above-described cover for microphone-equipped earphone (mouth-ear cover 100) shown in FIG. 15 of requiring at least one hand and fingertip to be used for retaining the fitted state.

For eliminating the inconvenience, the mouth-ear cover 100, as the cover for microphone-equipped earphone of EXAMPLE 2, shown in each of FIGS. 6 to 14 has a headphone-type band-like engagement tool 19 extending from the upper end of the ear cover section 21, to be worn by the user across the parietal region, so as to reach a position near the ear on the other side of the user. This allows the mouth-ear cover 100 to be fitted to the mouth and the ears of the face extremely stably while allowing both hands to be used by the user freely.

Figure 16:
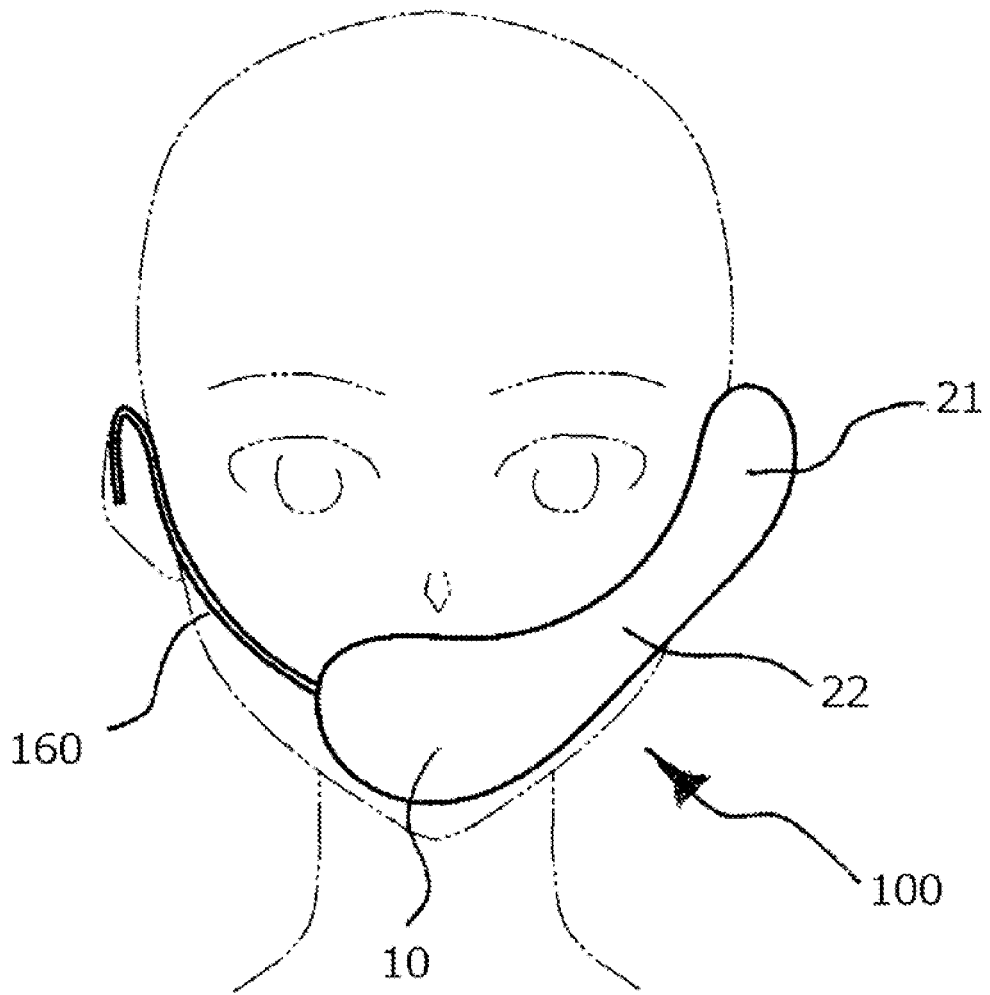
FIG. 16 depicts a front view of the mouth-ear cover according to EXAMPLE 2 provided with a glass-temple-like engagement tool.

Further, the mouth-ear cover 100 as the cover for microphone-equipped earphone shown in FIG. 16 has a glass-temple-like engagement tool 160 extending from the mouth cover section 20, to be worn by the user, so as to be hooked on the ear on the other side of the user. As a result of hooking the glass-temple-like engagement tool 160 and the hook 211 of the ear cover section 21 on the corresponding ones of the right-side and left-side ears, the mouth-ear cover 100 could be fitted to the mouth and the ears of the face extremely stably, while allowing both hands to be used by the user freely.

Figure 17:
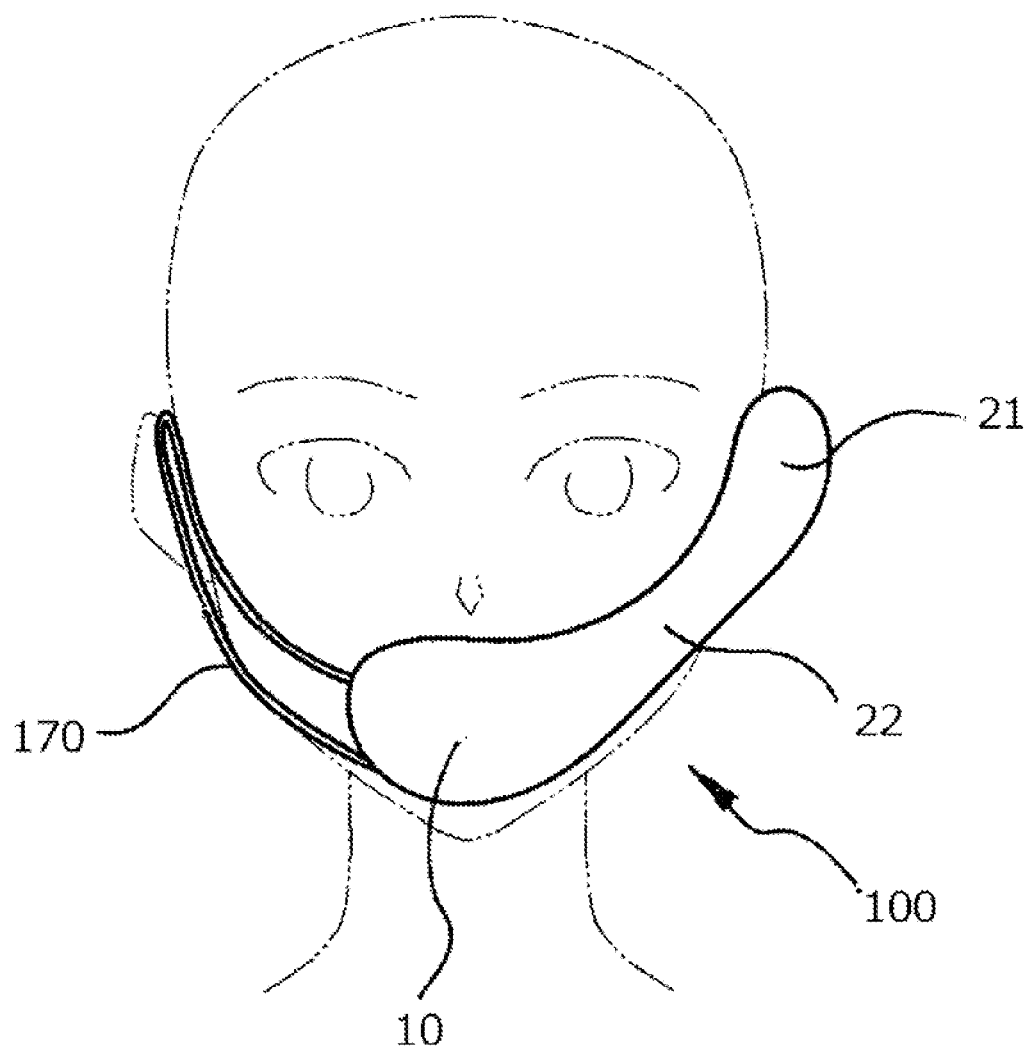
FIG. 17 depicts a front view of the mouth-ear cover according to EXAMPLE 2 provided with a mask-string-like engagement tool.

Still further, the mouth-ear cover 100 as the cover for microphone-equipped earphone shown in FIG. 17 has a mask-string-like engagement tool 170 extending from the mouth cover section 20, to be worn by the user, so as to be hooked on the ear on the other side of the user. As a result of hooking the mask-string-like engagement tool 170 and the hook 211 of the ear cover section 21 on the corresponding ones of the right-side and left-side ears, the mouth-ear cover 100 could be fitted to the mouth and the ears of the face extremely stably, while allowing both hands to be used by the user freely.

INDUSTRIAL APPLICABILITY

The present invention is widely applicable as a cover for microphone-equipped earphone to be used for communication equipment.

REFERENCE NUMERALS

10 Mouth cover
11 Microphone (microphone-equipped earphone)
12 Earphone (microphone-equipped earphone)
14 Internal space (mouth cover)
15 Pinching projection
16 Glass-temple-like engagement tool
17 Mask-string-like engagement tool
19 Headphone-type band-like engagement tool
20 Mouth cover section
21 Ear cover section
22 Voice passage section
100 Mouth-ear cover
140 Internal space (mouth cover section)
160 Glass-temple-like engagement tool
170 Mask-string-like engagement tool
210 Internal space (ear cover section)
211 Hook (ear cover section)
220 Voice passage (voice passage section)

What is claimed is:

1. A cover for microphone-equipped earphone having a microphone integral to an earphone to be used for communication equipment, the cover comprising:
    a mouth-ear cover for covering a mouth while allowing speaking of a user as well as covering one-side ear of the user into which the earphone is to be inserted, wherein the mouth-ear cover having a mouth cover section and an ear cover section is configured such that:
        an internal space defined by the mouth cover section of the mouth-ear cover has a substantially hemispherical shape capable of covering the mouth of the user, and has an edge of an opening thereof capable of closely contacting a periphery of the mouth;
        an internal space defined by the ear cover section of the mouth-ear cover has a substantially semi-oval spherical shape capable of covering the one-side ear of the user, and has an edge of an opening thereof capable of closely contacting a periphery of the one-side ear; and
        the internal space defined by the mouth cover section and the internal space defined by the ear cover section are capable of communicating with each other via a voice passage through which voice of the user is conveyable therebetween.

2. The cover for microphone-equipped earphone according to claim 1, wherein
    the voice passage has a semicircular shape, in cross section transverse to a longitudinal direction thereof, whose both ends are capable of abutting on a face of the user.

3. The cover for microphone-equipped earphone according to claim 2, wherein
    the mouth-ear cover has a hook, to be hooked on an upper end of the one-side ear of the user, provided at an upper end of the internal space defined by the ear cover section.

4. The cover for microphone-equipped earphone according to claim 2, further comprising:
    a headphone-type band-like engagement tool to be worn by the user across a parietal region to reach a position near the other-side ear of the user.

5. The cover for microphone-equipped earphone according to claim 2, further comprising:
    a glass-temple-like engagement tool extending from the mouth cover section to be hooked on the other-side ear of the user.

6. The cover for microphone-equipped earphone according to claim 2, further comprising:
    a mask-string-like engagement tool extending from the mouth cover section to be hooked on the other-side ear of the user.

7. The cover for microphone-equipped earphone according to claim 2, further comprising:
    a pinching projection arranged to project from an external surface of the mouth cover section.

8. The cover for microphone-equipped earphone according to claim 1, wherein
    the voice passage has a tubular shape penetrating an interior of a cover member of said cover.

9. The cover for microphone-equipped earphone according to claim 8, wherein
    the mouth-ear cover has a hook, to be hooked on an upper end of the one-side ear of the user, provided at an upper end of the internal space defined by the ear cover section.

10. The cover for microphone-equipped earphone according to claim 8, further comprising:
    a headphone-type band-like engagement tool to be worn by the user across a parietal region to reach a position near the other-side ear of the user.

11. The cover for microphone-equipped earphone according to claim 8, further comprising:
    a glass-temple-like engagement tool extending from the mouth cover section to be hooked on the other-side ear of the user.

12. The cover for microphone-equipped earphone according to claim 8, further comprising:
    a mask-string-like engagement tool extending from the mouth cover section to be hooked on the other-side ear of the user.

13. The cover for microphone-equipped earphone according to claim 8, further comprising:
   a pinching projection arranged to project from an external surface of the mouth cover section.

14. The cover for microphone-equipped earphone according to claim 1, wherein
   the mouth-ear cover has a hook, to be hooked on an upper end of the one-side ear of the user, provided at an upper end of the internal space defined by the ear cover section.

15. The cover for microphone-equipped earphone according to claim 1, further comprising:
   a headphone-type band-like engagement tool to be worn by the user across a parietal region to reach a position near the other-side ear of the user.

16. The cover for microphone-equipped earphone according to claim 1, further comprising:
   a glass-temple-like engagement tool extending from the mouth cover section to be hooked on the other-side ear of the user.

17. The cover for microphone-equipped earphone according to claim 1, further comprising:
   a mask-string-like engagement tool extending from the mouth cover section to be hooked on the other-side ear of the user.

18. The cover for microphone-equipped earphone according to claim 1, further comprising:
   a pinching projection arranged to project from an external surface of the mouth cover section.

\* \* \* \* \*